US009095428B2

(12) United States Patent
Kabir et al.

(10) Patent No.: US 9,095,428 B2
(45) Date of Patent: Aug. 4, 2015

(54) ARTIFICIAL HEART SYSTEM (71) Applicants: Omar M. Kabir, Waller, TX (US);
Ronald W. Webb, Houston, TX (US);
Mark A. Patterson, Houston, TX (US);
Gerrit M. Kroesen, Friendswood, TX (US); John C. Etcheverry, Houston, TX (US); Daniel B. Baxter, Tomball, TX (US); Robert Small, Williamsville, NY (US)

(72) Inventors: Omar M. Kabir, Waller, TX (US);
Ronald W. Webb, Houston, TX (US);
Mark A. Patterson, Houston, TX (US);
Gerrit M. Kroesen, Friendswood, TX (US); John C. Etcheverry, Houston, TX (US); Daniel B. Baxter, Tomball, TX (US); Robert Small, Williamsville, NY (US)

(73) Assignee: Cameron International Corporation, Houston, TX (US)

( * ) Notice: Subject to any disclaimer, the term of this patent is extended or adjusted under 35 U.S.C. 154(b) by 264 days.

(21) Appl. No.: 13/912,957

(22) Filed: Jun. 7, 2013

(65) Prior Publication Data
US 2013/0331934 A1 Dec. 12, 2013

Related U.S. Application Data (60) Provisional application No. 61/657,459, filed on Jun. 8, 2012.

(51) Int. Cl.
*A61F 2/24* (2006.01)
*A61M 1/10* (2006.01)
*F04D 13/06* (2006.01)
*F04D 29/46* (2006.01)
*A61M 1/12* (2006.01)

(52) U.S. Cl.
CPC .................. *A61F 2/24* (2013.01); *A61M 1/101* (2013.01); *A61M 1/1015* (2014.02); *A61M 1/122* (2014.02); *F04D 13/0606* (2013.01); *F04D 29/466* (2013.01)

(58) Field of Classification Search
CPC ... A61M 1/101; A61M 1/122; A61M 1/1015; A61M 1/1017
USPC ....................................................... 623/3.11
See application file for complete search history.

(56) References Cited

U.S. PATENT DOCUMENTS

| 5,873,696 | A | 2/1999 | Harada et al. |
| 6,220,832 | B1 | 4/2001 | Schöb |
| 6,463,324 | B1 * | 10/2002 | Ben-Haim et al. ................. 607/9 |
| 6,595,743 | B1 * | 7/2003 | Kazatchkov et al. ...... 415/171.1 |

(Continued)

FOREIGN PATENT DOCUMENTS

WO 97/35096 9/1997

OTHER PUBLICATIONS

Thomas, International Search Report and Written Opinion for PCT/US2013/044779, mailed Sep. 9, 2013.

*Primary Examiner* — Suzette J Gherbi
(74) *Attorney, Agent, or Firm* — Eubanks PLLC (57) ABSTRACT An artificial heart with a centrifugal pump is disclosed. In one embodiment, the artificial heart includes an impeller disposed in a housing. The impeller is configured to rotate to circulate blood through the housing. The impeller may include a set of blades on a first side of the impeller and a set of vanes on a second side opposite the first. The blades on the first side and the vanes on the second side allow blood circulation from both the first and the second sides of the impeller. The artificial heart may also or instead include a diffuser with adjustable vanes that enable variation in the output characteristics of the artificial heart pump. Various other artificial hearts, pumps, systems, and methods, including control systems and methods, are also disclosed.

13 Claims, 12 Drawing Sheets

(56) References Cited

U.S. PATENT DOCUMENTS

| | | |
|---|---|---|
| 6,949,066 B2 | 9/2005 | Bearnson et al. |
| 8,157,539 B2 * | 4/2012 | Hidaka et al. ............... 417/353 |
| 2006/0253194 A1 * | 11/2006 | Dial ............................ 623/3.13 |
| 2007/0253842 A1 * | 11/2007 | Horvath et al. ............. 417/350 |
| 2010/0069847 A1 * | 3/2010 | LaRose et al. .............. 604/151 |
| 2010/0168848 A1 * | 7/2010 | Horvath et al. ............. 623/3.13 |
| 2011/0098807 A1 * | 4/2011 | Frazier et al. ............... 623/3.16 |
| 2011/0301403 A1 * | 12/2011 | LaRose et al. ............... 600/16 |
| 2011/0313517 A1 * | 12/2011 | Reichenbach et al. ....... 623/3.11 |
| 2012/0095280 A1 * | 4/2012 | Timms ........................ 600/16 |
| 2012/0150291 A1 * | 6/2012 | Aber et al. .................. 623/3.14 |
| 2012/0245680 A1 * | 9/2012 | Masuzawa et al. .......... 623/3.11 |
| 2012/0310036 A1 * | 12/2012 | Peters et al. ................. 600/16 |
| 2012/0328460 A1 * | 12/2012 | Horvath et al. ............. 417/420 |
| 2014/0155998 A1 * | 6/2014 | Wampler ..................... 623/3.13 |

* cited by examiner

ARTIFICIAL HEART SYSTEM

BACKGROUND

This section is intended to introduce the reader to various aspects of art that may be related to various aspects of the presently described embodiments. This discussion is believed to be helpful in providing the reader with background information to facilitate a better understanding of the various aspects of the present embodiments. Accordingly, it should be understood that these statements are to be read in this light, and not as admissions of prior art.

The human body, like that of other animals, depends on oxygen for survival. Humans and many other animals have circulatory systems for delivering oxygen (among other things) to cells in the body. Taking the human body as an example, the human heart pumps oxygenated blood through blood vessels to the cells. As may be appreciated, natural human hearts typically enable both pulmonary circulation (generally, the flow of blood to and from the lungs to allow oxygenation of the blood) and systemic circulation (generally, the delivery of oxygen-rich blood to and return of oxygen-poor blood from cells) by pumping the blood through blood vessels with repeated contractions.

But like many other organs, the heart is susceptible to disease and failure. In some instances, a patient may be diagnosed with a heart defect so severe that a new heart is the recommended treatment. While transplants of natural hearts have been performed for decades, such a procedure requires a suitable donor heart. And patients waiting for new hearts greatly outnumber suitable donors. Artificial hearts may be used to sustain patient life, whether serving as a permanent replacement or as a bridge to a later heart transplant. Artificial hearts may include a centrifugal pump that drives the blood through a patient's circulatory system. Given the physiological importance of the circulatory system, improvements in artificial heart technology may directly lead to improved patient outcomes and quality of life.

SUMMARY

Certain aspects of some embodiments disclosed herein are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

Embodiments of the present disclosure generally relate to artificial hearts. In one embodiment, an artificial heart includes a rotating impeller to pump blood. Blades on one side of this impeller are configured to circulate blood away from that side of the impeller. But the impeller of this embodiment also includes vanes on an opposite side of the impeller, and these vanes pump blood away from this opposite side. Such an arrangement may reduce stagnation of blood near the opposite side, reducing the chances that blood clots will form. The vanes on the opposite side of the impeller may also be configured to balance the thrust force on the impeller from the blades. And in some embodiments, an artificial heart includes movable diffuser vanes that may be adjusted to alter output characteristics of the artificial heart.

Various refinements of the features noted above may exist in relation to various aspects of the present embodiments. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. Again, the brief summary presented above is intended only to familiarize the reader with certain aspects and contexts of some embodiments without limitation to the claimed subject matter.

BRIEF DESCRIPTION OF THE DRAWINGS

These and other features, aspects, and advantages of certain embodiments will become better understood when the following detailed description is read with reference to the accompanying drawings in which like characters represent like parts throughout the drawings, wherein.

DETAILED DESCRIPTION OF SPECIFIC EMBODIMENTS

One or more specific embodiments of the present disclosure will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments, the articles "a," "an," "the," and "said" are intended to mean that there are one or more of the elements. The terms "comprising," "including," and "having" are intended to be inclusive and mean that there may be additional elements other than the listed elements. Moreover, any use of "top," "bottom," "above," "below," other directional terms, and variations of these terms is made for convenience, but does not require any particular orientation of the components.

Figure 1:
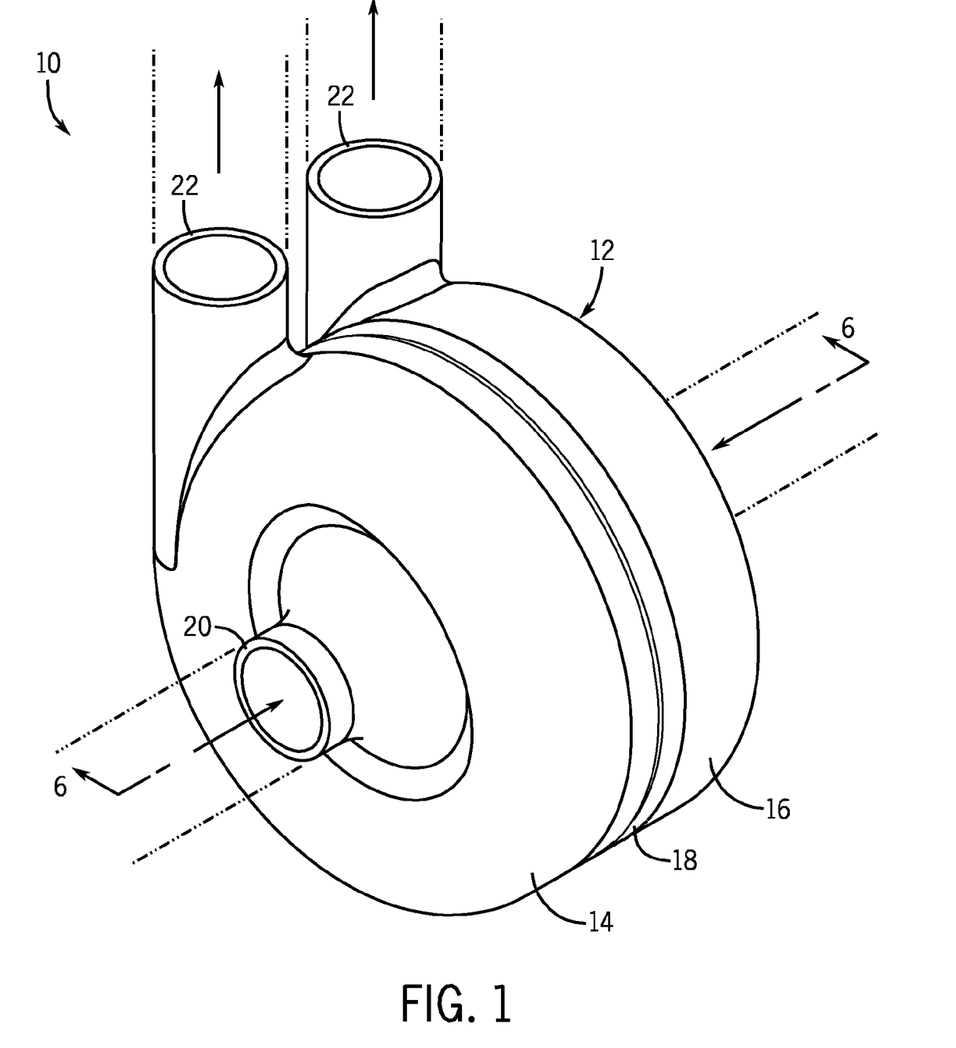
FIG. 1 is a perspective view of a dual-pump artificial heart in accordance with an embodiment of the present disclosure.

Turning now to the drawings, an artificial heart 10 is illustrated in FIG. 1 by way of example. As depicted, the artificial heart 10 includes a housing 12 having hollow shells 14 and 16 positioned opposite one another about an annular divider 18. The components of the housing 12 may be formed of any suitable materials, such as titanium. The artificial heart 10 is a dual-pump artificial heart in which pumps in the shells 14 and 16 receive blood from inlets 20 and drive the blood out from outlets 22.

Figure 2:
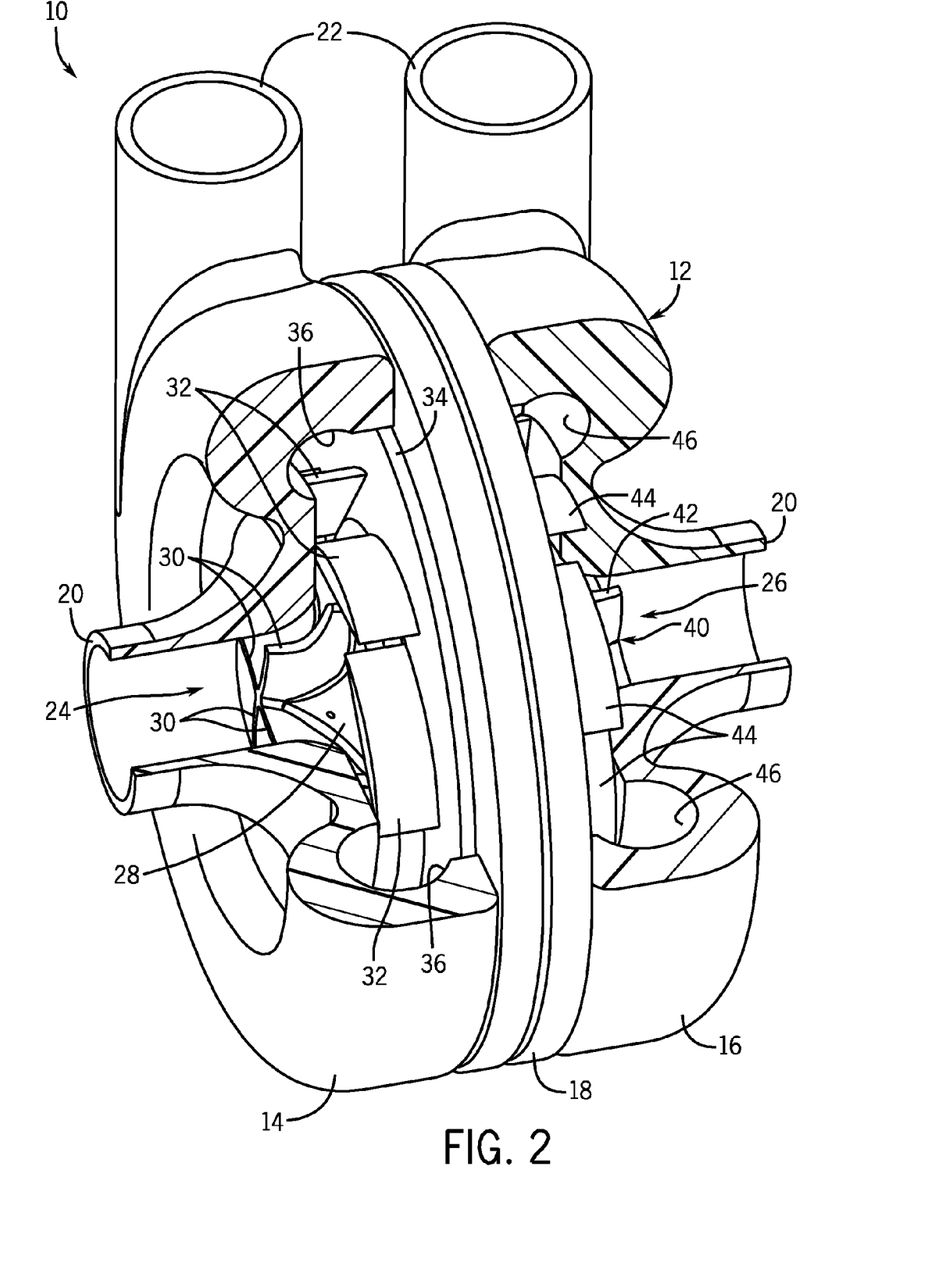
FIG. 2 is a sectional view of the dual-pump artificial heart of FIG. 1 depicting pump components, including diffusers and motor-driven impellers, in accordance with one embodiment.

Examples of such pumps are depicted in FIG. 2 in accordance with one embodiment. Particularly, a pump 24 is positioned inside the shell 14 to pump blood through one side of the artificial heart 10 and a pump 26 is positioned inside the shell 16 to pump blood through the other side. The artificial heart 10 may operate to provide both systemic and pulmonary circulation in a patient. For instance, the pump 24 may draw oxygen-poor blood (also referred to as deoxygenated blood) from the body through an inlet 20 and pump that blood from the outlet 22 to a patient's lungs for oxygenation. The pump 26, in turn, may draw the then oxygen-rich blood from the patient's lungs through the other inlet 20 and distribute the blood to the body via the other outlet 22.

The pumps 24 and 26 are depicted as continuous-flow, centrifugal pumps that enable steady circulation of blood from the pumps, in contrast to a natural heart that beats to pulse blood through the circulatory system. Consequently, such artificial hearts with continuous-flow pumps may also be referred to as "beat-less" hearts. But in other embodiments, an artificially generated pulse of desired amplitude may be created by varying the main driver speed in an oscillatory manner. The pump 24 includes an impeller 28 that rotates in operation to cause blood to flow between the inlet 20 and outlet 22 of shell 14. Blades 30 on the front of the impeller accelerate blood received from the inlet 20 and direct the blood in a radially outward direction to diffuser vanes 32 on a disk 34. The diffuser vanes 32 generally increase the efficiency of the pump 24 and control flow pressure in a fluid passage 36 leading to the outlet 22. As described in further detail below, the diffuser vanes 32 in some embodiments are adjustable in position to enable variation in the output flow characteristics of the pump 24.

As depicted in FIG. 2, the pump 26 is similar to the pump 24 in design and operation. Particularly, the pump 26 includes an impeller 40 having blades 42. The pump 26 generally receives blood from inlet 20 of shell 16 and routes the blood through diffuser vanes 44 on a disk (which may be like disk 34), through a fluid passage 46, and out from the outlet 22 of the shell 16. In the present embodiment, the pump 24 is configured for clockwise flow through the diffuser vanes 32 and the fluid passage 36 (when considered from the perspective of one looking down the inlet 20 of the shell 14 to the impeller 28), while the pump 26 is configured for counter-clockwise flow through the diffuser vanes 44 and the fluid passage 46 (when considered from the perspective of one looking down the inlet 20 of the shell 16 to the impeller 40). To accommodate such a difference, and as here depicted, various features of the impellers and diffusers (e.g., the direction of blades and vanes) of the two pumps may be opposite one another to promote the desired rotational flow of each pump. In at least one embodiment, one of the pumps (e.g., pump 26) is configured to have slightly larger capacity and pressure capabilities than the other pump (e.g., pump 24) to account for differences in pulmonary and systemic circulatory characteristics in a patient.

Figure 3:
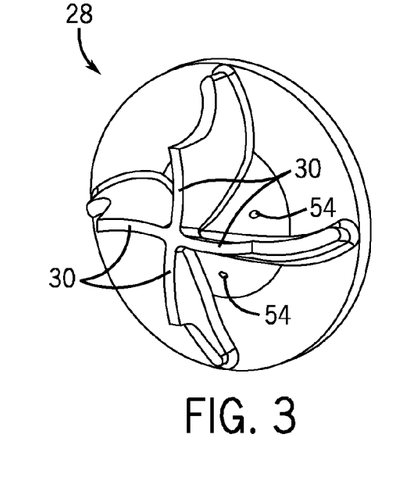
FIG. 3 is a front perspective view of the impeller of FIG. 2, which includes a set of blades on the front of the impeller for pumping blood through the artificial heart and a set of through holes to maintain flow of fresh blood to the back of the impeller.
Figure 4:
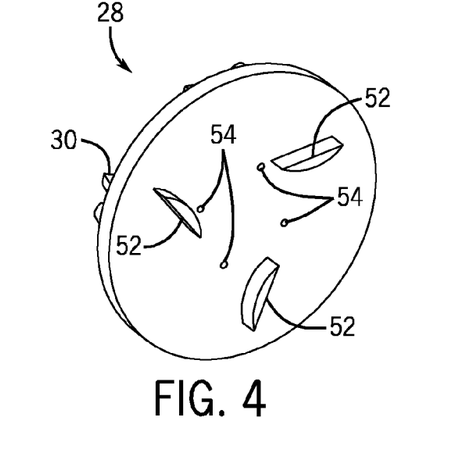
FIG. 4 is a rear perspective view of the impeller of FIGS. 2 and 3, which includes a set of vanes on the back of the impeller also for pumping blood through the artificial heart.

Additional features of the impellers of the pumps 24 and 26 may be better understood with reference to FIGS. 3 and 4, which depict an impeller 28 in accordance with one embodiment. As noted above, the impeller 28 includes a set of blades 30 on what may be referred to as the front face of the impeller 28 (i.e., the side facing the inlet 20 of the shell 14 in the assembled heart 10). But in addition to these blades 30, the impeller 28 also includes "pump-out" vanes 52 on a rear face of the impeller 28 that provide several advantages over other artificial heart pump designs.

At least some previous continuous-flow, centrifugal heart pumps have been configured in a way that may cause blood behind impeller to become stagnant or to recirculate in the areas behind the impellers and near other internal surfaces rather than flow out of the pumps. Further, some previous centrifugal heart pumps include drivers (e.g., motors) having bearing tubes that are open to the pump chamber, allowing blood to enter and potentially become stagnant in the bearing tubes. And the impellers of some centrifugal heart pumps have been designed such that the hydrodynamic thrust forces on the impellers are not balanced, potentially causing gyroscopic motion of the artificial hearts during operation. But the inclusion of the presently-disclosed pump-out vanes 52 may address any or all of these problems.

Particularly, the pump-out vanes 52 serve as a second continuous-flow device (in addition to the blades 30), which promotes continuous flow of blood from the back of the impeller 28 to the diffuser vanes 32 and reduces the potential of stagnation of blood behind the impeller 28. In at least some embodiments, fluid communication holes 54 (which may also be referred to as through holes) further promote continuous flow from the back of the impeller 28 by allowing fresh blood to be drawn from the front of the impeller 28 through the communication holes 54. The pump-out vanes 52 may also draw blood from any open, blood-containing recesses behind the impeller 28, such as from an exposed bearing tube of a motor for driving the impeller 28. And in at least one embodiment, the pump-out vanes 52 are designed to balance the thrust force on the impeller 28 generated from the rotation of the blades 30. Or stated differently, during operation the pump-out vanes 52 on the back of the impeller 28 generate a thrust force on the impeller 28 that is equal in magnitude to and opposite in direction from the thrust force generated by the blades 30 on the front of the impeller 28. This in turn allows the impeller to operate in a thrust-free force condition that reduces or eliminates the potential of gyroscopic forces that could develop in previous artificial heart pumps. Additionally, in at least some embodiments the communication holes 54 are configured to accelerate blood flowing through the holes 54 to inhibit coagulation of the blood and clogging within the holes.

Figure 5:
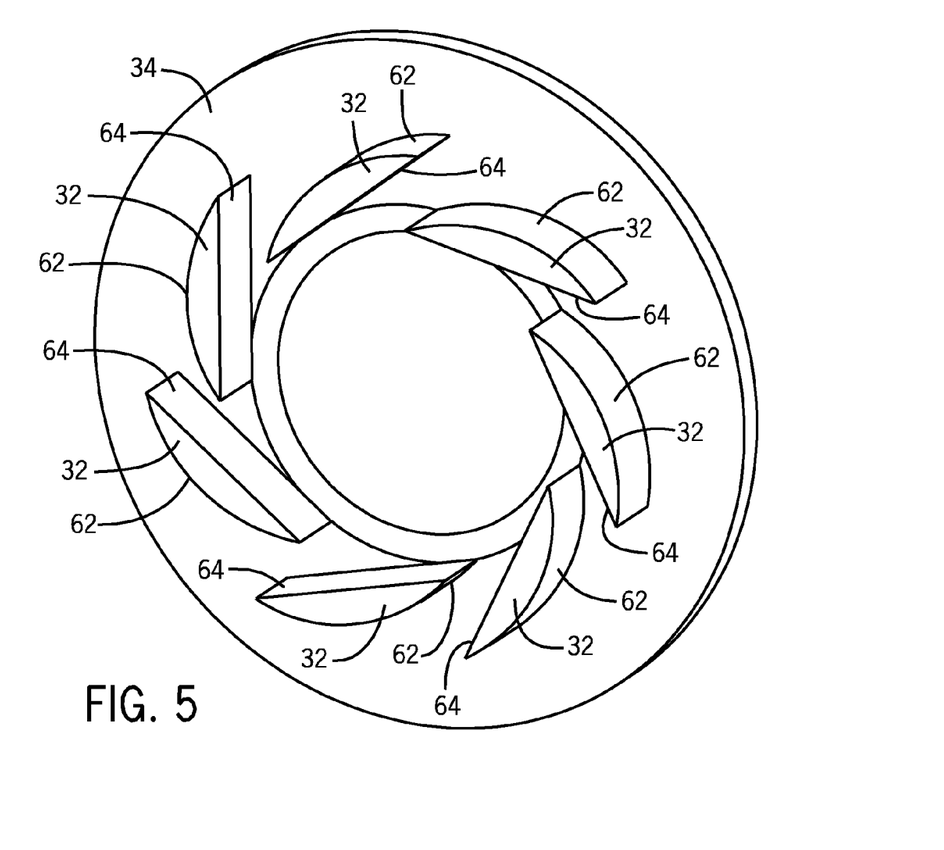
FIG. 5 depicts an embodiment of a diffuser including vanes for routing blood from the impeller.

Rotation of the impeller 28 causes blood to flow to the diffuser vanes 32, which are depicted in FIG. 5, along with the disk 34, as removed from the artificial heart 10 by way of example. In the presently depicted embodiment, each diffuser vane 32 includes a radially outward surface 62 and a radially inward surface 64. In operation, blood flow from the impeller 28 is routed outwardly through openings between the surfaces 62 and 64 of adjacent diffuser vanes 32. The diffuser vanes 32 generally provide an increasing area of flow for blood as it passes between the surfaces 62 and 64, which converts some kinetic energy of the fluid (proportional to blood velocity) into potential energy (corresponding to blood pressure head). In other words, the diffuser vanes 32 slow the flow velocity and increase the flow pressure of the blood.

The particular impeller and diffuser depicted in FIGS. 3-5 are provided as examples, but other embodiments may differ in design. For instance, the number and configuration of the blades 30, the diffuser vanes 32, the pump-out vanes 52, and the communication holes 54 may differ as desired for a given application. The shapes and sizes of the components of the impeller and the diffuser may also vary. In the embodiment depicted in FIG. 2, the impeller 40 and the diffuser vanes 44 are similar to the impeller 28 and the diffuser vanes 32 described above. But the positions of the fluid communication holes 54 through the impeller 40 and the directions of the blades 42 and pump-out vanes 52 of the impeller 40 and of the diffuser vanes 44 are reversed to accommodate the counter-clockwise flow from pump 26, as described above. Of course, other embodiments may exhibit additional differences between these components.

Figure 6:
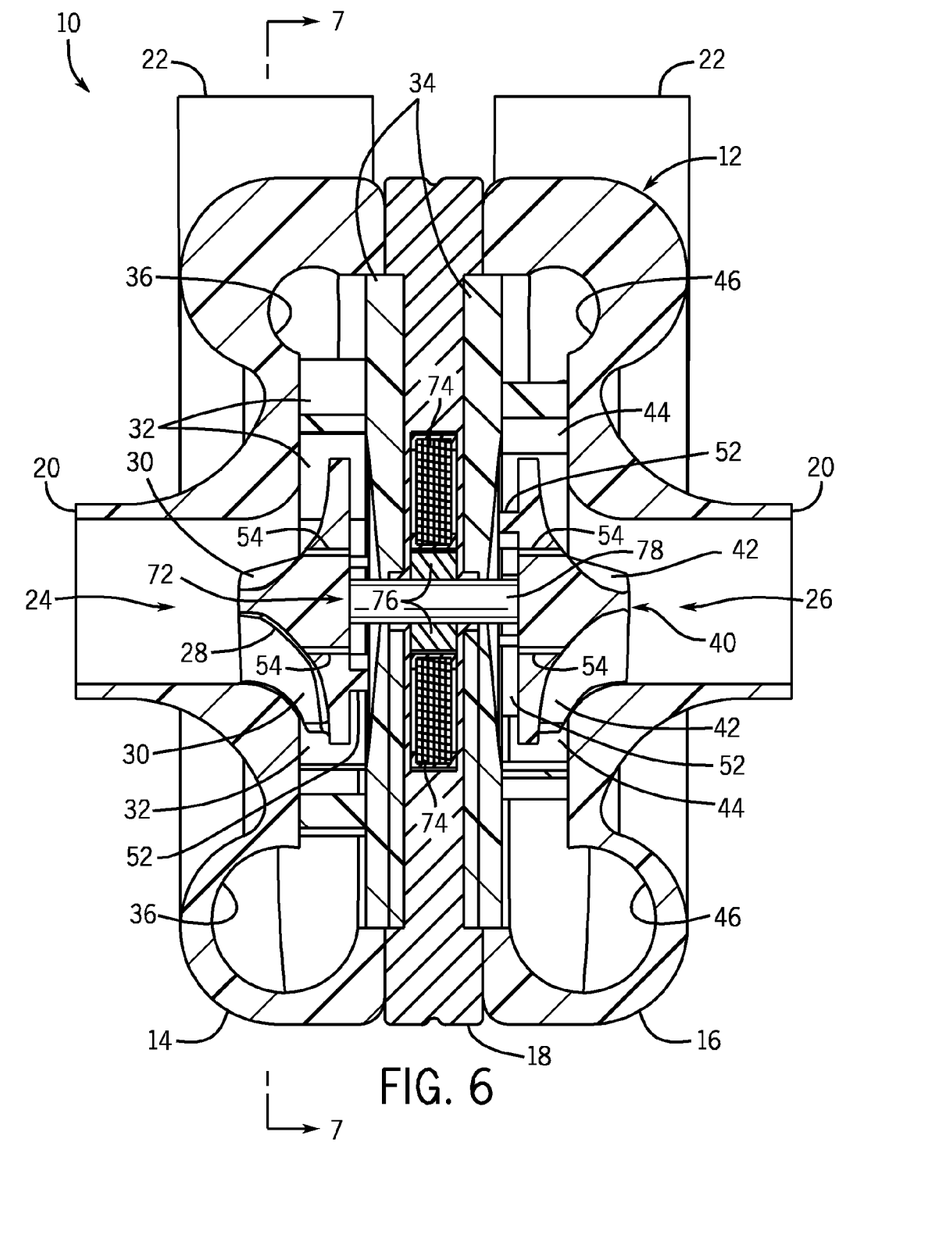
FIG. 6 is a cross-section of the dual-pump artificial heart of FIG. 1 and depicts additional internal components of the heart in accordance with one embodiment.

In an embodiment depicted in FIG. 6, the impellers 28 and 40 in the artificial heart 10 are driven by a motor 72 within the annular divider 18. In this embodiment, the motor 72 includes a stator 74 (e.g., a motor winding) for driving a rotor 76 coupled to a shaft 78. The rotor 76 may include one or more permanent magnets—such as an annular arrangement of magnets about the shaft 78—that rotate the shaft 78 in response to a changing electromagnetic field generated from the stator 74. In such an embodiment, the magnets may act also as a magnetic bearing in which the rotor 76 and the shaft 78 levitate in the center of the stator 74 due to magnetic forces. A magnetically operated thrust bearing may also be included to guard against over-thrust of the rotor and pump failure. The shaft 78 is coupled to both impellers of the heart such that rotation of the shaft 78 causes the clockwise and counter-clockwise motion of the impellers as discussed above. Although the motor 72 is common to both impellers 28 and 40 in the depicted embodiment, it is noted that in other embodiments two separate motors 72 may be provided to independently drive each impeller 28 and 40. In such embodiments, the pair of independent motors 72 could be provided back-to-back within the annular divider 18.

The motor 72 (or motors 72) may be any suitable motor, such as a brushless, direct-current motor. In other embodiments, the motor 72 may instead be a self-energized motor such as piezoelectric motor energized by any motion (including human motion) or a sound-energy-converting motor. As described in greater detail below, a controller may be provided to control operation of the motor 72. Additionally, in at least some embodiments the motor 72 not only supplies mechanical power to the pump, but also provides adequate energy to charge a set of high density batteries (which may be integrated into the controller or provided separately) for power storage to be used in the event of the motionless condition of a human or animal patient (e.g., during sleep). In this case, the battery set can maintain the motor drive speed for continued operation of the artificial heart. Given the criticality of the artificial heart to a patient, the battery set may include redundant batteries and the system may be operated with the goal of keeping at least one of the batteries fully charged at all times, while allowing charging of any other batteries.

Figure 7:
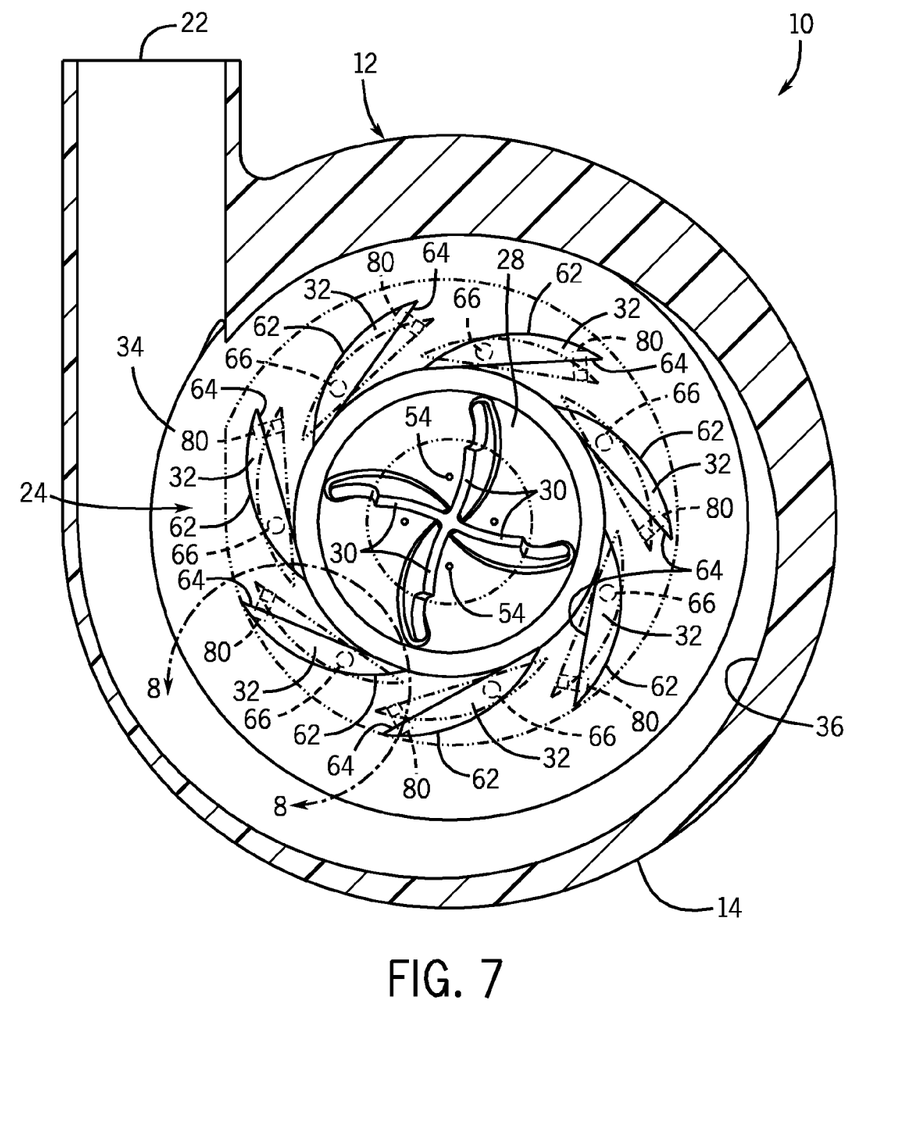
FIG. 7 is another cross-section of the dual-pump artificial heart of FIGS. 1 and 6 and depicts the diffuser vanes as having an adjustable position in accordance with one embodiment.

As discussed above, and as may be better understood with reference to FIG. 7, rotation of the impeller 28 within the shell 14 causes blood to flow outwardly to the diffuser vanes 32. And the diffuser vanes 32 cause the blood to generally flow in a clockwise direction within the curved fluid passage 36 inside the shell 14 to the outlet 22. The impeller 40 and diffuser vanes 44 act similarly, causing blood to generally flow in a counter-clockwise direction within the curved passage 46 of the shell 16 to its corresponding outlet 22 (see FIGS. 2 and 6). While certain impellers are depicted in the figures by way of example, it will be appreciated that the impellers may vary in shape and size. For instance, in various embodiments, the impellers could take the form of radial, axial, or mixed flow impellers, and the blades on the impellers (e.g., blades 30) may have any suitable curvature, such as a backward lean of fifteen to seventy-five degrees.

Figure 8:
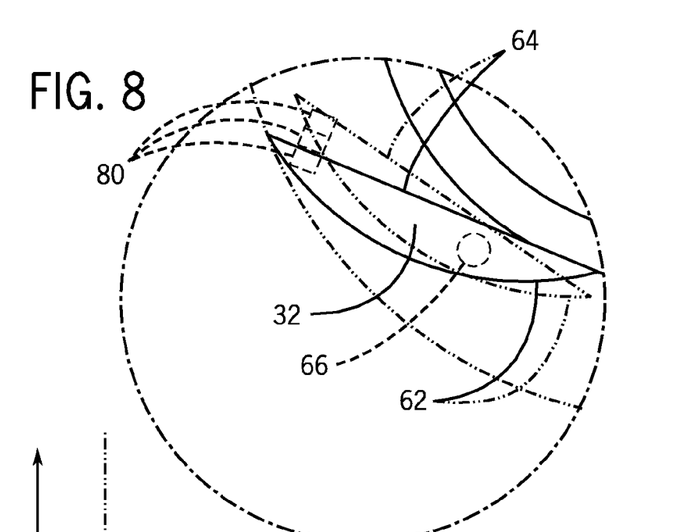
FIG. 8 is a detail view of a diffuser vane of FIG. 7 and illustrates an embodiment in which the position of the diffuser vane may be magnetically controlled.

Moreover, in some embodiments the diffuser vanes 32 and 44 are adjustable to change the performance characteristics of the pumps 24 and 26 (e.g., to better match the performance of the pumps to the blood requirements of the patient). For example, as depicted in FIGS. 7 and 8, the positions of the diffuser vanes 32 are adjustable by moving the vanes 32 about rotational axes defined by pivots 66. The diffuser vanes 44 may be similarly adjustable. In one embodiment, the positions of the diffuser vanes may be magnetically controlled by magnets 80. These magnets 80 may be installed in any suitable position, such as within or behind the disks to which the diffuser vanes are attached. For example, in the embodiment depicted in FIG. 8, a series of electromagnets 80 may be positioned relative to a diffuser vane 32 such that activation of a particular electromagnet 80 in the series draws the diffuser vane 32 into a desired position. In this manner the diffuser vanes 32 can be rotated into different positions about the pivots 66 to vary the resistance of the diffuser to blood flow by varying the size of openings between the diffuser vanes 32. And such variation of size enables variation in output characteristics of the pump 24 (e.g., the flow speed and pressure of pumped blood), even during operation of the pump 24 in a patient. Although FIGS. 7 and 8 generally depict a series of three magnets 80 for each diffuser vane (thus enabling adjustment of each vane between three different positions), a smaller or greater number of magnets (and potential positions for the respective diffuser vanes) may be used in other embodiments.

Figure 9:
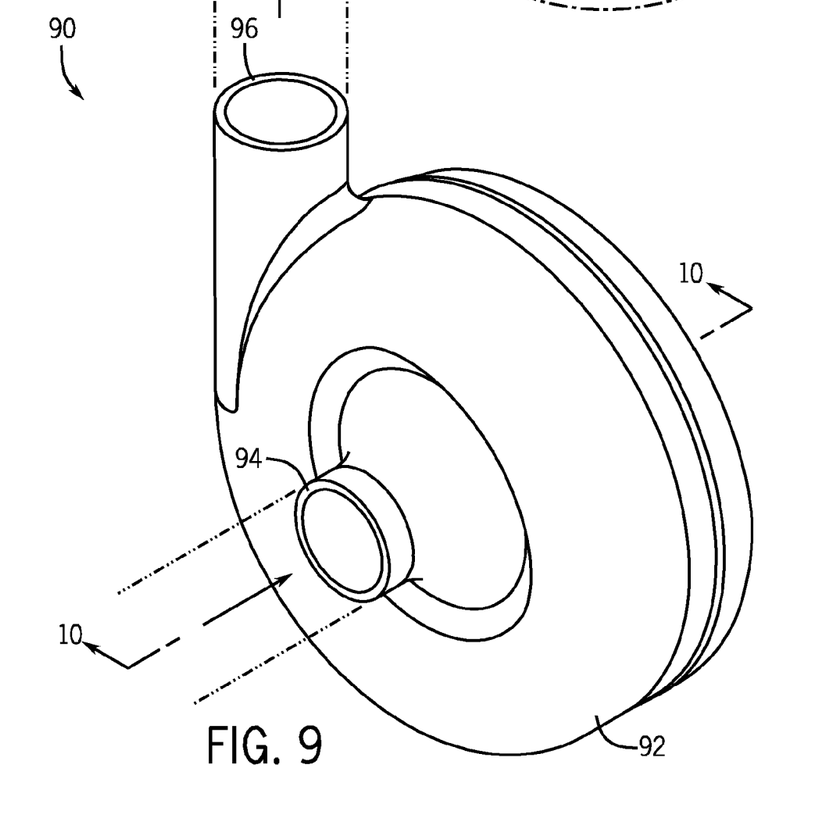
FIG. 9 is a perspective view of a single-pump artificial heart in accordance with one embodiment.
Figure 10:
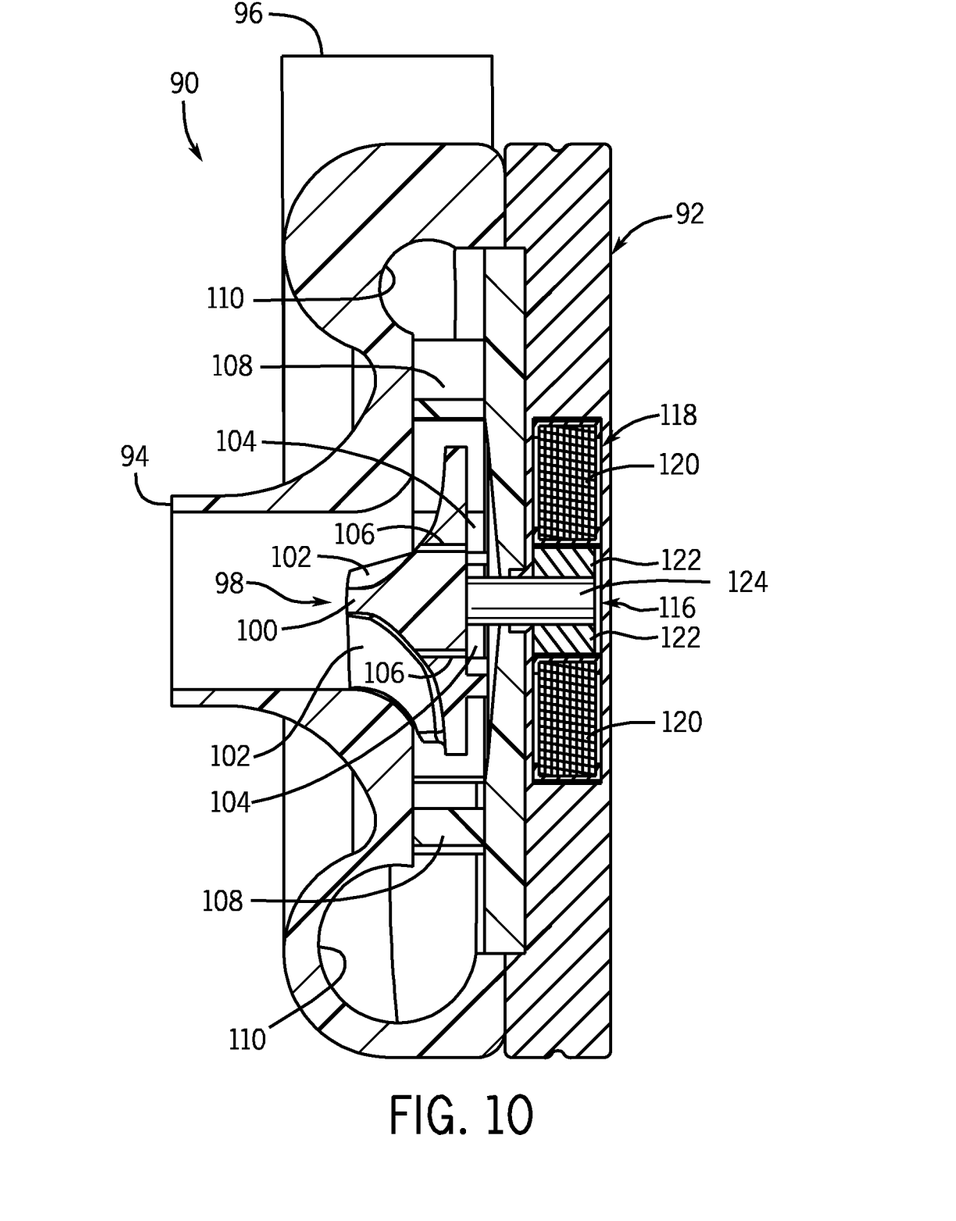
FIG. 10 is a cross-section of the single-pump artificial heart of FIG. 9 and depicts internal components of the artificial heart in accordance with one embodiment.

While artificial heart 10 has been depicted as a dual-pump heart, many of the features described above may also be included in a single-pump design, such as the artificial heart 90 depicted in FIGS. 9 and 10 in accordance with one embodiment. The artificial heart 90 includes a housing 92 having an inlet 94 and an outlet 96. A centrifugal pump 98 is installed within the housing 92 and operates in a manner similar to that described above with respect to pump 24. Indeed, in the embodiment depicted in FIGS. 9 and 10 the pump 98 is identical to the pump 24, although the two pumps may vary in other embodiments.

The depicted pump 98 includes an impeller 100 having blades 102, pump-out vanes 104, and fluid communication holes 106 to circulate fresh blood through the pump-out vanes 104 behind the impeller 100, through diffuser vanes 108, and into the fluid passage 110 of the heart 90. A cavity 116 in the housing 92 includes a motor 118 for driving the impeller 100. Similar to that discussed above with respect to FIG. 6, the motor 118 includes a stator 120 (e.g., a motor winding), a rotor 122 (e.g., one or more permanent magnets), and a shaft 124 that transmits rotation of the rotor 122 to the impeller 100. The motor type, charging, and control system for the single-pump artificial heart 90 may be similar to that described above with respect to the dual-pump artificial heart 10. Namely, the motor 118 may be any suitable motor, such as a brushless, direct-current motor; a self-energized motor, such as piezoelectric motor energized by any motion (including human motion); or a sound-energy-converting motor. And in some embodiments, the motors of single-pump artificial hearts may also provide charging energy to one or more batteries that may be used to provide subsequent operational power when patients having the artificial hearts are at rest.

The pump-out vanes 104 may provide benefits similar to that described above with respect to pump-out vanes 52. Namely, the vanes 104 may be configured to increase circulation and reduce blood stagnation behind the impeller 100, to draw blood out from the cavity 116 (e.g., from an annulus between the stator 120 and the rotor 122), and to balance thrust forces on the impeller 100 from the blades 102 to reduce or eliminate potential gyroscopic motion of the pump 98. And this balancing of thrust forces of the blades 102 and the pump-out vanes 104 and reduction in gyroscopic motion increases flexibility of an artificial heart system by allowing the use of a single-pump artificial heart alone or the use of a pair of single-pump artificial hearts rather than a dual-pump artificial heart.

Figure 11:
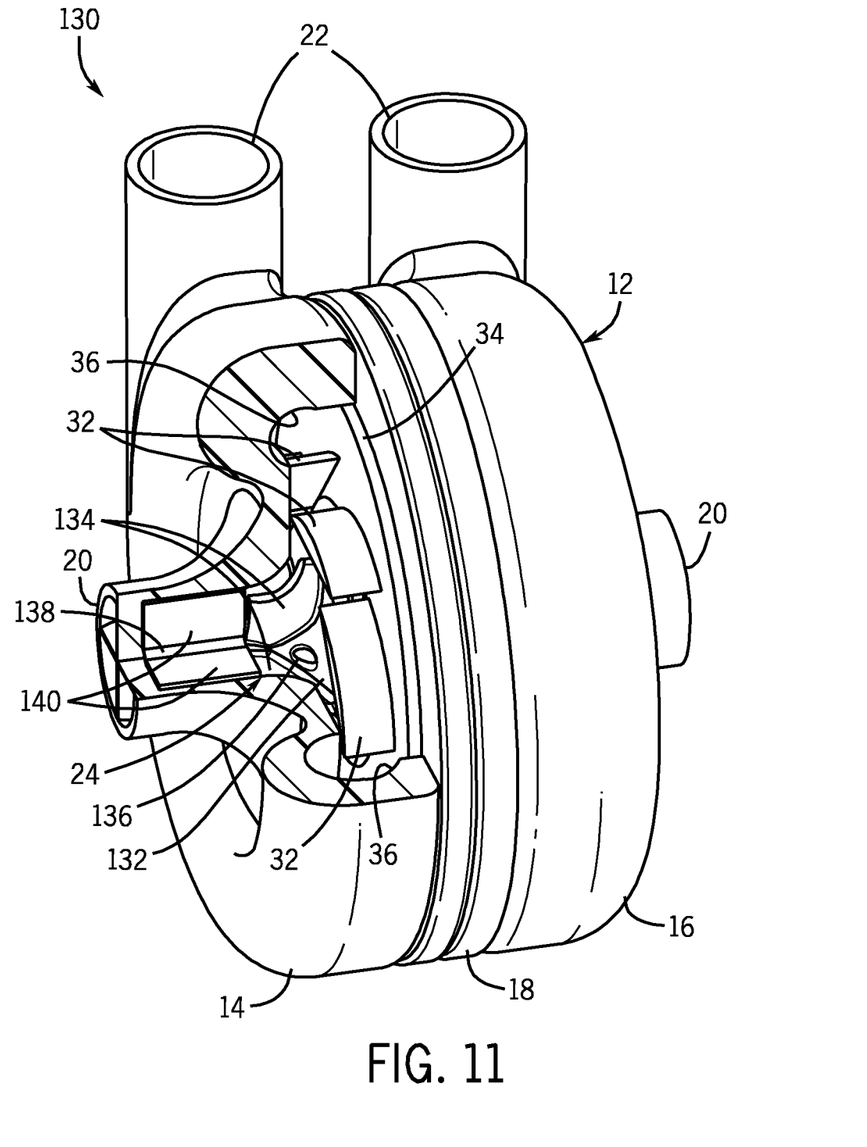
FIG. 11 is a perspective view of a dual-pump artificial heart of another embodiment having an impeller that differs from that of the heart of FIG. 2.
Figure 12:
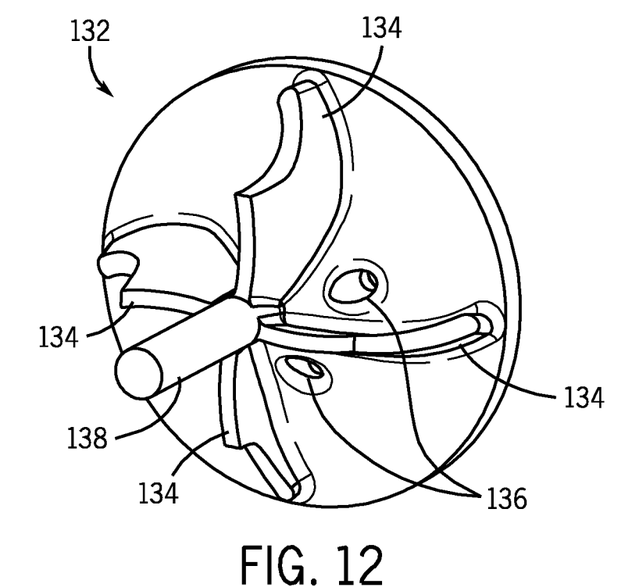
FIGS. 12-14 depict the impeller of FIG. 11 in greater detail in accordance with one embodiment.
Figure 13:
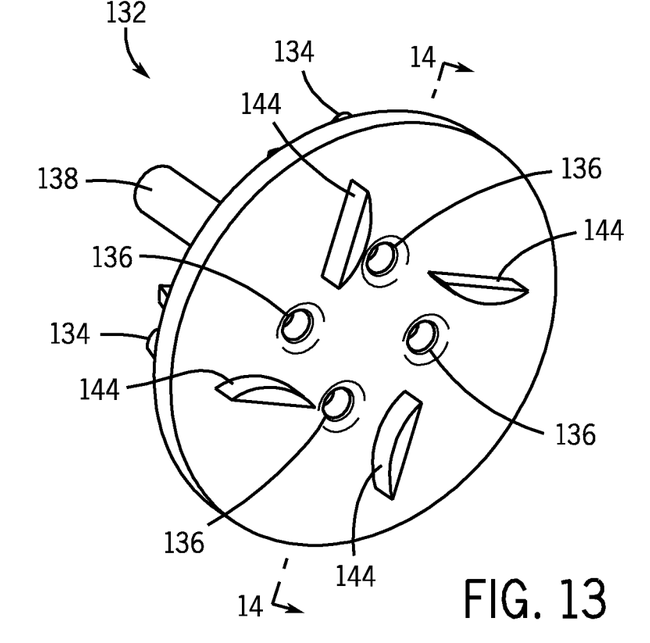
Figure 14:
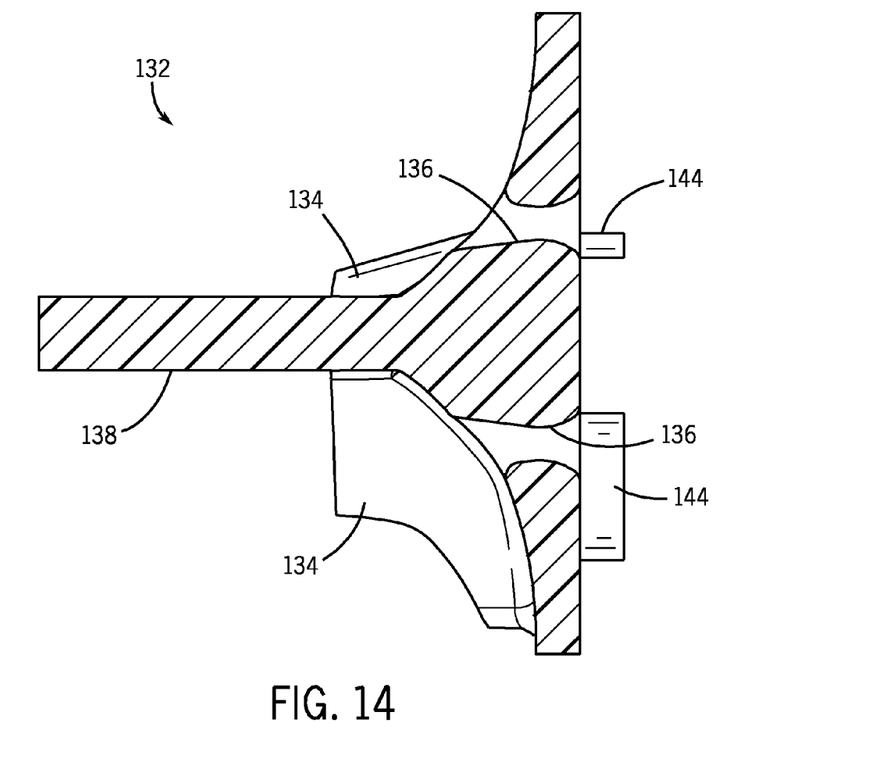

Another example of a dual-pump artificial heart is depicted in FIG. 11. This artificial heart 130 is generally similar to the artificial heart 10 above, but includes an impeller 132 that differs from the impeller 28. Although only one impeller 132 is depicted in the present figure, it is noted that a second impeller 132 may also be provided within the shell 16. Various features of the impeller 132 are depicted in FIGS. 12-14. The impeller 132 includes blades 134 that route fluid radially outward (e.g., toward diffuser vanes 32) and communication holes 136 that enable fluid to flow through to a rear side of the impeller 132. The communication holes 136 may be contoured to accelerate blood passing through the holes 136 and inhibit clogging. The housing 12 of the heart 130 includes a magnetic bearing in the form of magnets 140 that receive an extension 138 of the impeller 132 to encourage proper alignment of the impeller 132 during operation. The rear face of the impeller 132 also includes pump-out vanes 144 that function similarly to pump-out vanes 52 described above.

Figure 15:
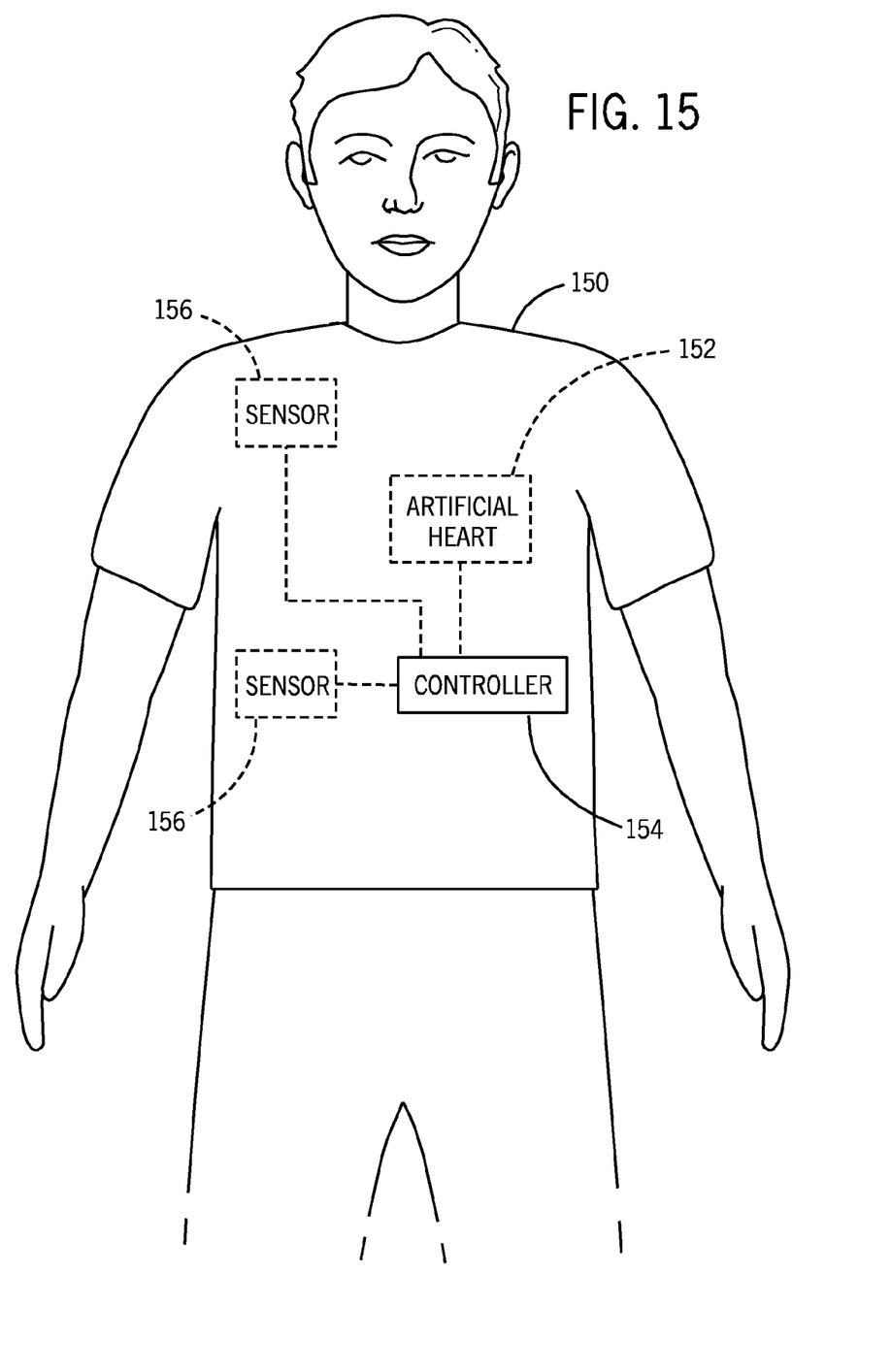
FIG. 15 is one example of an artificial heart system including an artificial heart implanted in a patient.

One example of an artificial heart system deployed in a patient 150 is provided in FIG. 15. The system includes an artificial heart 152 implanted in the patient 150 to circulate blood through the patient. Although the patient 150 is depicted as a human patient, artificial hearts have been implanted in other animals and the techniques and devices disclosed herein are not limited to use with humans. In some embodiments, the artificial heart 152 may be identical to the dual-pump artificial heart 10, the single-pump artificial heart 90, or the other dual-pump artificial heart 130. In other embodiments, the artificial heart 152 may include a pair of single-pump artificial hearts 90 or may include one or more artificial hearts that differ from hearts 10, 90, and 130. The blood may be circulated continuously through the patient in a beat-less manner, or the motor speed of the artificial heart may be oscillated to generate a pulsating flow.

The system includes a controller 154 for controlling operation of the artificial heart 152. The controller 154 may include any suitable hardware (e.g., processor, memory, storage, and input-output interface) and programming for providing such control. Non-limiting examples of operational aspects of the artificial heart 152 that may be governed by the controller 154 include motor speed and, if the artificial heart 152 includes adjustable diffuser vanes, the position of the diffuser vanes. The controller 154 may also include a power source to transmit power to the pump motor inside the artificial heart 152. For example, the power source may be a battery set charged by the motor (as noted above) or some other battery. Although the controller 154 is depicted as separate from the heart 152, it is noted that the controller 154 could be integrated with the heart 152 in some embodiments.

The controller 154 may receive data from one or more sensors and control operation of the artificial heart based on the data. For instance, as depicted in FIG. 15, the artificial heart system includes two sensors 156. These sensors 156 may be internal sensors—which may be artificial sensors or natural, physiological body sensors (e.g., neurons, ganglia, or nerves)—embedded in the patient 150 (either as part of the artificial heart 152 itself or, as here depicted, separate from the artificial heart 152). The sensors may instead be external sensors placed on the patient 150. The sensors 156 collect physiological data from the patient, such as blood pressure and temperature. Artificial sensors 156 may communicate with the controller 154 wirelessly or they may be connected to the controller 154 with wires. Further, "natural" sensors 156 (e.g., neurons, ganglia, or nerves) may communicate with the controller through a neural interface. For example, signals may be routed to the brain of a patient via the patient's nervous system, and the brain may send control signals through the nervous system that may be received and interpreted by the controller 154 via a neural interface. While artificial sensors may become clogged over time, natural sensors generally avoid such a problem.

Figure 16:
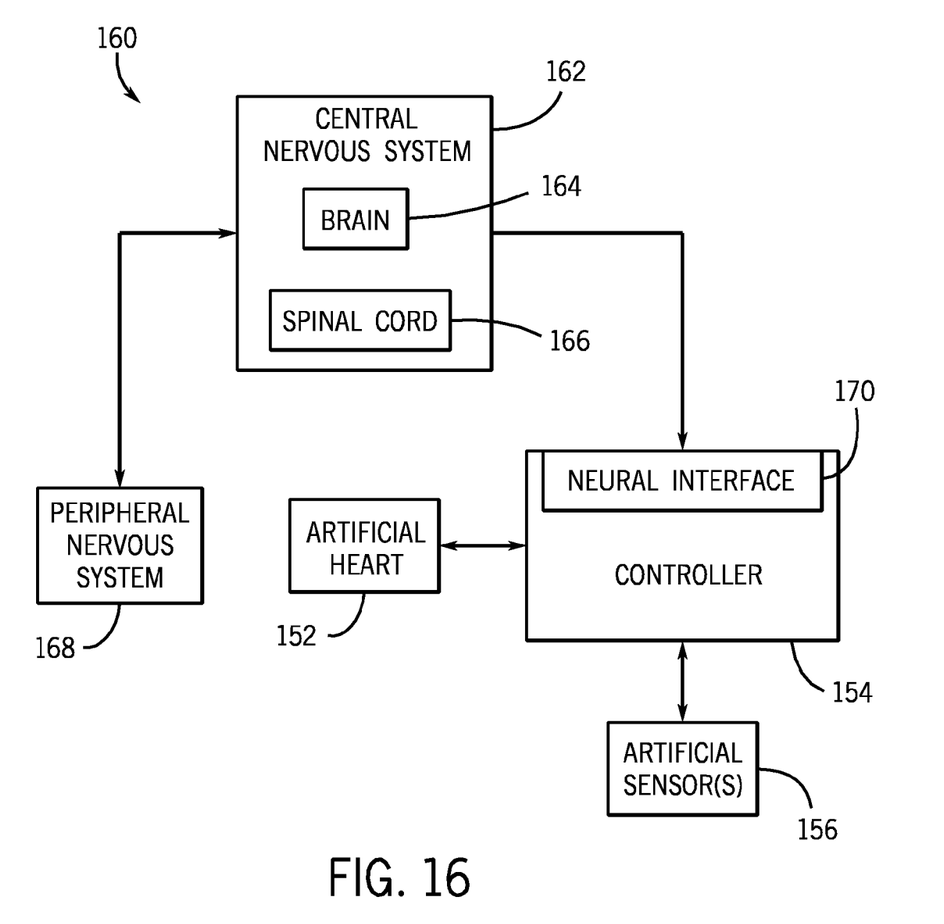
FIG. 16 is a block diagram depicting incorporation of the artificial heart system of FIG. 15 with the nervous system of a patient in accordance with one embodiment.

One example of a biological—artificial hybrid control system is generally represented by block diagram 160 in FIG. 16. The central nervous system 162 of a patient includes the brain 164 and the spinal cord 166. The central nervous system 162 receives communications from the peripheral nervous system 168 (including for example neurons, ganglia, and nerves) that are indicative of bodily sensations and physiological data. In an ordinary person having a natural human heart, the brain 164 processes the communications from the peripheral nervous system and generates control signals that are routed through signal pathways of the peripheral nervous system to the heart to govern its operation (e.g., pumping speed). In the presently depicted embodiment having an artificial heart, the control signals from the brain 164 may be routed (e.g., generally through the same signal pathways of the peripheral nervous system that were connected to the natural heart) to a neural interface 170 of the controller 154. Such an interface may be provided in a manner similar to that known and currently used in the field of limb prosthetics. But it is noted that this hybrid system of an artificial controller and heart operating based on signals from a patient's nervous system may require a change in the implantation procedure for the artificial heart. Particularly, unlike the current practice of implanting an artificial heart in which neural pathways connecting the natural heart to the brain are severed and wasted, the neural pathways may instead be connected to the neural interface 170 during implantation of the artificial heart to enable command signals from the brain 162 to be received and interpreted by the controller 154.

The system (e.g., via the controller 154) may use the physiological patient data to monitor, and in some instances adjust, operation of the artificial heart 152. For instance, by monitoring physiological data of the patient 150 via the sensors 156, the controller 154 may detect changes in the physiological data indicative of a change in the resistance of a patient's circulatory system (e.g., increased resistance due to physical exertion or decreased resistance due to relaxation). In one embodiment, in response to the detected change in measured physiological data, the controller can vary the output characteristics of the artificial heart 152 during operation by varying the motor speed (for coarse output adjustments) or the position of diffuser vanes in the pump (for fine output adjustments). The position of the diffuser vanes may be adjusted in any suitable manner, including by magnetic adjustment in the manner described above.

In some embodiments the controller 154 is a smart system that adjusts output characteristics of the artificial heart 152 based on stored data (e.g., a lookup table) of desired output characteristics for the patient 150. Particularly, in one embodiment, the controller 154 stores data indicative of desired output characteristics based on at least one physical characteristic of the patient (e.g., height or weight) and the currently measured physiological data. Further, the controller 154 may be programmed with numerous algorithms to distinguish various modes of operating conditions of patient activities and may use these algorithms to make smart decisions regarding the supply of blood flow to adjust the blood flow characteristics to that desired for the given mode. In one embodiment, the system will be preprogrammed with a number of physician-approved scenarios for maintaining the desired blood flow range. The controller 154 may also learn, through operation, as it runs into special cases and it adds the special cases to its existing intelligent system. An example of this system would be when the patient walks upward, on an inclined surface, the system maintains a higher range of desired blood flow and, conversely, in the case of a patient sleeping it maintains lower blood flow. But in the case of sleeping, if the ambient temperature is also colder than normal it may be desirable to keep blood flow within a higher range than at warmer ambient temperatures and the system can be programmed to respond accordingly by maintaining blood flow within the higher range so the patient does not feel as though something is wrong with his or her body. Consequently, this system allows operation of the artificial heart 152 on a customized basis in which output performance is specifically tailored to a patient's physical attributes and current physiological state and requirements. And in some embodiments, the controller 154 may detect trends in the measured physiological data and adjust the output characteristics of the heart 152 in anticipation of future needs of a patient (e.g., higher blood pressure during patient exertion).

Furthermore, in hybrid control systems that also rely on patient's nervous system for controlling the artificial heart 152, the controller 154 may be used to receive biological command signals from the brain 164, via the neural interface 170 (which may also include signal conditioners), and provide an appropriate command signal to the artificial heart 152 (or multiple hearts 152) to control motor speed, diffuser vane positions, battery charging, or other functionality. In this case these artificial components may be fully controlled by the patient's brain as though the real heart is functioning. In such an embodiment, the permanent and pertinent neural interface system and sensors of the patient's original biological heart's receiving system may be functioning and communicating without any significant changes being made during the implanting of the artificial heart. Neural pathways that communicate command signals from the brain to the heart may be connected to the controller 154, allowing the brain 164 to be the main control system (in conjunction with controller 154) for controlling the artificial heart system to process and provide desired blood flow by adjusting one or both of the main driver(s) speed and the position of the diffuser guide vanes to achieve the required blood flow.

While the aspects of the present disclosure may be susceptible to various modifications and alternative forms, specific embodiments have been shown by way of example in the drawings and have been described in detail herein. But it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An artificial heart system comprising:
an artificial heart housing;
an impeller configured to pump blood through the artificial heart housing;
a plurality of adjustable diffuser vanes that enable variation in output characteristics of the artificial heart; and
a sensor configured to measure physiological data of a person.

2. The artificial heart system of claim 1, wherein the artificial heart housing and the sensor are embedded in the body of the person.

3. The artificial heart system of claim 1, wherein the artificial heart system is configured to change the positions of the adjustable diffuser vanes during operation based on the physiological data measured by the sensor.

4. The artificial heart system of claim 1, wherein each diffuser vane of the plurality of adjustable diffuser vanes is configured to rotate about a respective axis in response to a magnetic force on the diffuser vane.

5. A method comprising:
circulating blood through a patient using an artificial heart implanted in the patient; and
changing output characteristics of the artificial heart during operation of the artificial heart, wherein changing output characteristics of the artificial heart during operation includes adjusting the position of a diffuser vane of the artificial heart during operation.

6. The method of claim 5, wherein adjusting the position of the diffuser vane of the artificial heart during operation includes magnetically adjusting the position of the diffuser vane during operation.

7. The method of claim 5, wherein adjusting the position of the diffuser vane is performed based on a change in physiological data measured from the patient in which the artificial heart is implanted.

8. A method comprising:
circulating blood through a patient using an artificial heart implanted in the patient; and
changing output characteristics of the artificial heart during operation of the artificial heart;
wherein circulating blood through the patient includes oscillating a motor speed of the artificial heart to produce a pulsating flow of blood through the patient.

9. The method of claim 5, wherein changing output characteristics of the artificial heart includes using a controller programmed to distinguish between various modes of operating conditions of patient activities, to make decisions regarding the supply of blood flow based on blood flow desired for the given mode, and to output a control signal to change the output characteristics of the artificial heart.

10. The method of claim 9, wherein the control signal from the controller commands a change in the speed of a motor to change the blood flow in the artificial heart or a change in the position of a diffuser vane to change the blood flow in the artificial heart.

11. A method comprising:
   circulating blood through a patient using an artificial heart implanted in the patient;
   changing output characteristics of the artificial heart during operation of the artificial heart; and
   receiving physiological signals at the brain of the patient and outputting a command signal from the brain to change the output characteristics of the artificial heart.

12. The method of claim 11, wherein outputting the command signal from the brain includes routing the command signal to a controller via a neural interface.

13. The method of claim 12, comprising interpreting the command signal from the brain with the controller and controlling the artificial heart with the controller to change the output characteristics of the artificial heart.

* * * * *